United States Patent
Cho et al.

(10) Patent No.: US 6,583,321 B1
(45) Date of Patent: Jun. 24, 2003

(54) 4'-METHANESULFONYL-BIPHENYL DERIVATIVES AS A HIGHLY SELECTIVE CYCLOOXYGENASE-2 INHIBITOR

(75) Inventors: Il Hwan Cho, Seoul (KR); Jee Woong Lim, Gyeonggi-do (KR); Ji Young Noh, Busan (KR); Jong Hoon Kim, Gyeonggi-do (KR); Sang Wook Park, Gyeonggi-do (KR); Hyung Chul Ryu, Gyeonggi-do (KR); Je Hak Kim, Gyeonggi-do (KR); Hyung Ok Chun, Gyeonggi-do (KR); So Young Wang, Seoul (KR); Eun Young Lee, Gyeonggi-do (KR)

(73) Assignee: Cheil Jedang Corporation, Seoul (KR)

( * ) Notice: Subject to any disclaimer, the term of this patent is extended or adjusted under 35 U.S.C. 154(b) by 0 days.

(21) Appl. No.: 10/264,113

(22) Filed: Oct. 3, 2002

(30) Foreign Application Priority Data

Oct. 10, 2001 (KR) ................................. 2001-0062491

(51) Int. Cl.⁷ ............................................. C07C 317/14
(52) U.S. Cl. ............................................ 568/33; 568/32
(58) Field of Search ........................... 568/28, 32, 33, 568/35

(56) References Cited

U.S. PATENT DOCUMENTS

| | | | | |
|---|---|---|---|---|
| 3,375,256 A | * | 3/1968 | Bach et al. | 546/232 |
| 3,804,904 A | * | 4/1974 | Bentley et al. | 568/37 |
| 3,878,240 A | * | 4/1975 | Kuenzy | 562/409 |
| 3,962,345 A | * | 6/1976 | Yukio et al. | 568/37 |
| 3,993,683 A | * | 11/1976 | Nickl et al. | 560/12 |
| 5,248,828 A | * | 9/1993 | Saito et al. | 568/33 |
| 5,284,978 A | * | 2/1994 | Kinishi et al. | 568/33 |
| 5,840,991 A | * | 11/1998 | Yeng et al. | 568/32 |

OTHER PUBLICATIONS

CA:125:300608 abs of WO9626921 Sep. 1996.*
CA:137:150265 abs of WO2002060378 Aug. 2002.*
CA:134:340518 abs of WO 2001032633 May 2001.*
CA:128:153923 abs of WO 9804508 Feb. 1998.*

* cited by examiner

*Primary Examiner*—Jean F. Vollano
(74) *Attorney, Agent, or Firm*—Swanson & Bratschun, L.L.C.

(57) ABSTRACT

The present invention relates to a novel 4'-methanesulfonyl-biphenyl derivative having a structure of formula 1 and its pharmaceutically acceptable salts as a highly selective cyclooxygenase-2 inhibitor.

<Formula 1>

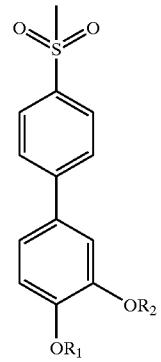

Formula 1

Wherein, $R^1$ and $R^2$ are defined in this specification respectively.

3 Claims, No Drawings

4'-METHANESULFONYL-BIPHENYL DERIVATIVES AS A HIGHLY SELECTIVE CYCLOOXYGENASE-2 INHIBITOR

TECHNICAL FIELD

The present invention relates to 4'-methanesulfonyl-biphenyl derivatives as a highly selective cyclooxygenase-2 inhibitor.

BACKGROUND

Most of non-steroid anti-inflammatory drugs represent actions such as anti-inflammation, analgesic, and antipyretic activity by inhibiting the enzymatic activity of cyclooxygenase or prostaglandin G/H synthase. In addition, they can suppress the uterine contraction induced by hormones and the cell proliferation in several kinds of cancers. First, only cyclooxygenase-1 was known to be found in cow as a constitutional enzyme. But recently, cyclooxygenase-2 is elucidated as an induced form. Cyclooxygenase-2 is identified to be discriminated clearly from cyclooxygenase-1 and can be provoked easily by mitogen, endotoxin, hormones, growth factors, cytokines and the like.

Prostaglandins have various pathological and physiological functions. Precisely, cyclooxygenase-1 as a constitutional enzyme participates in the secretion of basic endogenous prostaglandin and plays an important role in physiological aspects such as stomach homeostasis, renal blood circulation and so on. On the other hand, cyclooxygenase-2 is induced by inflammatory factors, hormones, growth factors, cytokines and the like and thus plays an important role in pathological effects of prostaglandins. Therefore, selective inhibitors against cyclooxygenase-2 are expected to have no side effect on account of the functional mechanism compared with the anti-inflammatory drugs such as conventional non-steroid agents and to represent actions such as anti-inflammation, analgesic, and antipyretic activity. Furthermore, it is estimated to suppress the uterine contraction induced by hormones and the cell proliferation in several kinds of cancers. Especially, it probably has less side effects such as gastrointestinal toxicity, renal toxicity and the like. Also, it is assumed to prevent the synthesis of contractive prostanoids and thus inhibit the contraction of smooth muscle induced by the prostanoid. Hence, it can be applied usefully to treat a premature birth, dysmenorrhea, asthma and several diseases associated with eosinophilic leukocytes. Besides, it can be exploited widely to cure osteoporosis, glaucoma and athymia, which has been disclosed in a lot of references, especially the usefulness of selective inhibitors against cyclooxygenase-2 (References: John Vane, "Towards a better aspirin" in *Nature*, Vol. 367, pp 215–216, 1994; Bruno Battistini, Regina Botting and Y. S. Bakhle, "COX-1 and COX-2; Toward the Development of More Selective NSAIDs" in *Drug News and Perspectives*, Vol. 7, pp 501–512, 1994; David B. Reitz and Karen Seibert, "Selective Cyclooxygenase Inhibitors" in *Annual Reports in Medicinal Chemistry*, James A. Bristol, Editor, Vol. 30, pp 179–188, 1995).

The selective inhibitors against cyclooxygenase-2 have been reported to have various structural forms. Among these, the diaryl heterocycle structure, namely a tricyclic system, has been studied most frequently and exploited to construct a lot of candidate substances. In this structure, it is essential that sulfonamide or methanesulfone group exist onto one phenyl group. The initial substance of such a structure is identified to be Dup697 (Bioorganic and Medicinal Chemistry Letters, Vol. 5, No. 18, p 2123, 1995). Then, as a derivative, SC-58635 (Journal of Medicinal Chemistry, Vol. 40, p 1347, 1997) having a pyrrazole structure, MK-966 (WO 95/00501) having a furanone structure and the like are disclosed.

DISCLOSURE OF INVENTION

Based upon the above technical backgrounds, the inventors of the present invention have tried a lot in order to develop novel compounds as a highly selective cyclooxygenase-2 inhibitor. As a result, we have found that 4'-methanesulfonyl-biphenyl derivatives of formula 1 satisfied such a purpose and completed the present invention successfully.

Therefore, the object of the present invention is to provide 4'-methanesulfonyl-biphenyl derivatives of formula 1 and its pharmaceutically acceptable salts as depicted below.

Hereinafter, the present invention will be described more clearly.

The present invention relates to 4'-methanesulfonyl-biphenyl derivatives of formula 1 and its pharmaceutically acceptable salts.

<Formula 1>

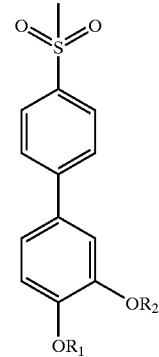

Formula 1

Wherein, $R^1$ and $R^2$ are respectively a hydrogen;
$C_1$–$C_4$-alkyl substituted or not substituted by halogens;
$C_3$–$C_7$-cycloalkyl;
$C_1$–$C_5$-alkyl containing 1~3 ether bonds and/or an aryl substitute;
substituted or not substituted phenyl;
or substituted or not substituted five or six ring-cycled heteroaryl containing more than one hetero atoms selected from a group consisting of nitrogen, sulfur and oxygen (wherein, phenyl or heteroaryl can be one- or multi-substituted by a substituent selected from a group consisting of hydrogen, methyl, ethyl and isopropyl).

The compound of the present invention can exist as a pharmaceutically acceptable salt form, wherein the pharmaceutically acceptable salt means a nontoxic salt containing organic salt and inorganic salt and accepted pharmaceutically. The inorganic salt consists of aluminum, ammonium, calcium, copper, iron, lithium, magnesium, manganese, potassium, sodium, zinc and the like and preferably, ammonium, calcium, magnesium, potassium, sodium. The organic salt consists of primary-, secondary- or tertiary-amines, naturally substituted amines, cyclic amines, modified salts prepared through basic ion exchange resin and the like. Preferably, the organic salt can be selected among arginine, betain, caffeine, colin, N,N- dibenzylethylenediamine, diethylamine, 2-diethylaminoethanol, 2-dimethylaminoethanol, ethanolamine, ethylenediamine, N-ethylmorpholin, N-ethylpiperidine, N-methylglucamine, glucamine, glucosamine, histidine, hydrapamine, N-(2-hydroxyethyl) piperidine, N-(2-hydroxyethyl)pyrrolidine, isopropylamine, lysine, methylglucamine, morpholin, piperazine, piperidine, polyamine resin, procain, purine, teobromine, triethylamine, trimethylamine, tripropylamine, tromethamine and the like.

Besides, the compound of the present invention can be a salt form of nontoxic acids containing the organic acid and the inorganic acid and accepted pharmaceutically, in case that it be basic. Preferably, the acid can be adopted among acetic acid, adipic acid, aspartic acid, 1,5-naphthalenedisulfonic acid, benzenesufonic acid, benzo acid, camposulfonic acid, citric acid, 1,2-ethanedisulfonic acid, ethanesulfonic acid, ethylendiaminetetraacetic acid, fumaric acid, glucoheptonic acid, gluconic acid, glutamic acid, hydriodic acid, hydrobromic acid, hydrochloric acid, icethionic acid, lactic acid, maleic acid, malic acid, manderic acid, methanesulfonic acid, music acid, 2-naphthalene disulfonic acid, nitric acid, oxalic acid, parnoic acid, pantothenic acid, phosphoric acid, pivalic acid, propionic acid, salicylic acid, stearic acid, succinic acid, sulfuric acid, tartaric acid, p-toluenesulfonic acid, undecanoic acid, 10-undecenoic acid and the like and more preferably, among succinic acid, hydrobromic acid, hydrochloric acid, maleic acid, methanesulfonic acid, phosphoric acid, sulfuric acid, tartaric acid and the like.

Preferably, the compound of the present invention of formula 1 as a selective inhibitor against cyclooxygenase-2 is that $R^1$ and $R^2$ are separately methyl, ethyl, propyl, isopropyl, butyl, cyclopropyl, cyclopentyl, or benzyl.

For preferred embodiments of the present invention, the compounds of formula 1 will be described more clearly as follows:

4'-methanesulfonyl-3,4-dimethoxy-biphenyl;
4'-methanesulfonyl-3,4-diethoxy-biphenyl;
4'-methanesulfonyl-3,4-dipropyloxy-biphenyl;
4'-methanesulfonyl-3,4-diisopropyloxy-biphenyl;
4'-methanesulfonyl-3,4-dicyclopropyloxy-biphenyl;
4'-methanesulfonyl-3,4-dibutyloxy-biphenyl;
4'-methanesulfonyl-3,4-dibenzyloxy-biphenyl;
4'-methanesulfonyl-3,4-dicyclopentyloxy-biphenyl; and
3-butoxy-4-isopropoxy-4'-methanesulfonyl-biphenyl On the other hand, the compounds of formula 1 in the present invention can be prepared by performing the procedures as illustrated below.

However, the process for preparing the compounds of the present invention will not be restricted to following descriptions, especially in reaction solvents, bases, amounts of used reactants and the like.

Moreover, the compound of the present invention also can be prepared by exploiting and combining various synthetic methods described in the present specification or disclosed in other references of those skilled in this arts with a coordinate and arbitrary mode.

Those skilled in the art will appreciate that the conceptions and specific embodiments disclosed in the foregoing description may be readily utilized as a basis for modifying or designing other embodiments.

Concretely, the compound of formula 1 in the present invention can be prepared by exploiting cathechol as an initial material as illustrated schematically in following reaction formula 1 and 2.

<Reaction Formula 1>

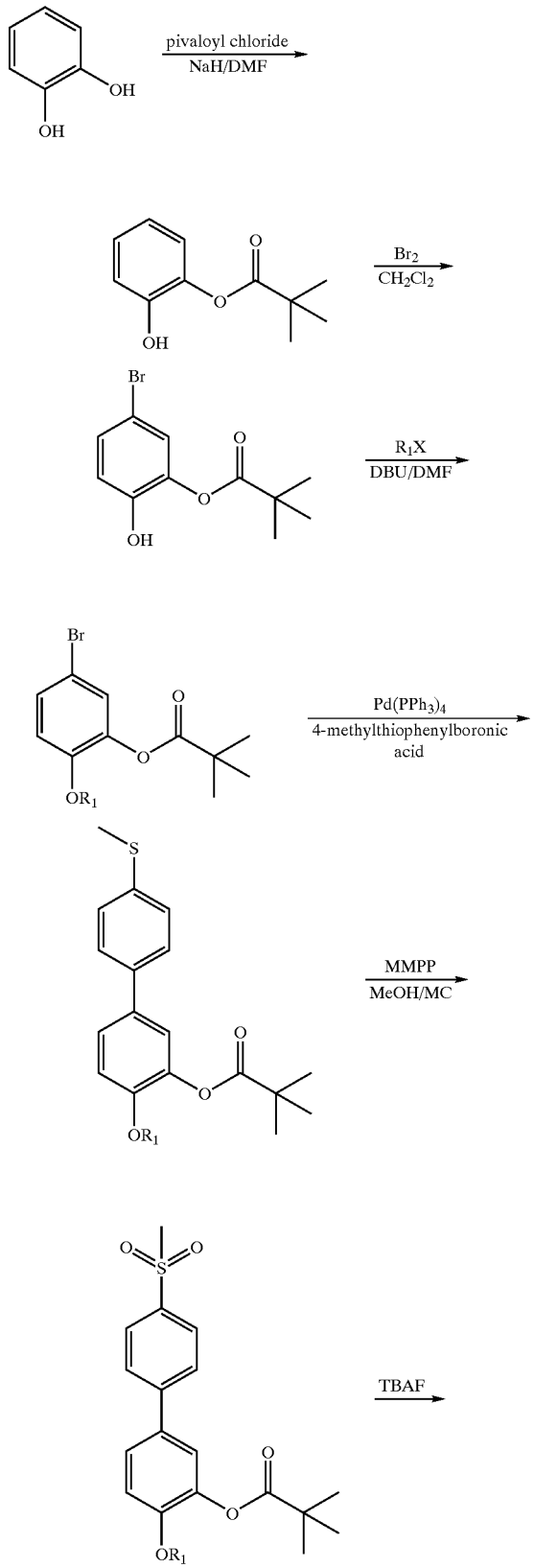

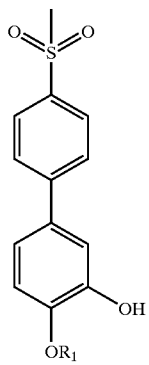

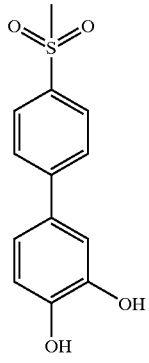

Wherein, R signifies $R^1$ and $R^2$, Formula (1a) represents that $R^1$ and $R^2$ are identical in the compound of formula 1.

In the process for the preparation of the present invention, it is most important to prepare a biphenyl intermediate through the Suzuki reaction after adopting a selective protecting group to cathechol, an initial substance.

In the process for adopting a selective protecting group to cathechol, an initial substance, the reaction solvent can be an organic solvent commonly used such as dichloromethane, chloroform, tetrahydrofurane, dimethylformamide, benzene, toluene, diethylether and the like and dimethylformamide is the most preferable among these. Tetrahydrofurane and diethylether are recommended to exploit with purifying. Resulting intermediate compound should be selectively brominated at the range of 0~−80° C. and more preferably, at a low temperature in between −75~−80° C. Catalyst which is used in Suzuki reaction to form biphenyl derivatives can be selected among palladiumacetate, tetrakistriphenylphosphinepalladium, and bistriphenylphosphinepalladium chloride and tetrakistriphenylphosphinepalladium is most preferable. The reaction should be progressed under the presence of inorganic salt group such as sodiumacetate, sodium hydroxide, potassium hydroxide, sodium carbonate, potassium carbonate and the like and potassium carbonate is most preferable among these. Additionally, benzene, tetrahydrofuran, toluene, dimethylformamide and the like are utilized as a solvent and benzene and toluene are most preferable. Oxidizing agent which is utilized in a process of oxidizing sulfanyl group included in biphenyl intermediate into sulfonyl group is mainly selected from OXONE, hydrogen peroxide, magnesium monoperoxyphthalate hexahydrate, metachloroperoxybenzoic acid and the like. There is no problem to exploit anything among these, but magnesium monoperoxyphthalate hexahydrate is most preferable.

In reaction formula 1, $R^1$ group is adopted to 4-location of biphenyl first, and then pivaloyl group to 3-location as a protecting group. In this case, pivaloyl group is seceded in the process of hydrolyzing methanesulfonyl group which has been formed onto 4'-location of biphenyl and then, $R^2$ group is adopted to 3-location of biphenyl. As a result, the compound of formula 1 where $R^1$ and $R^2$ are mutually different is obtained.

In reaction formula 2, t-butyldimethylsilyl group is adopted to 4-location of biphenyl as a protecting group and pivaloyl group to 3-location as a protecting group. In this case, both t-butyldimethylsilyl group and pivaloyl group are Reaction Formula 2

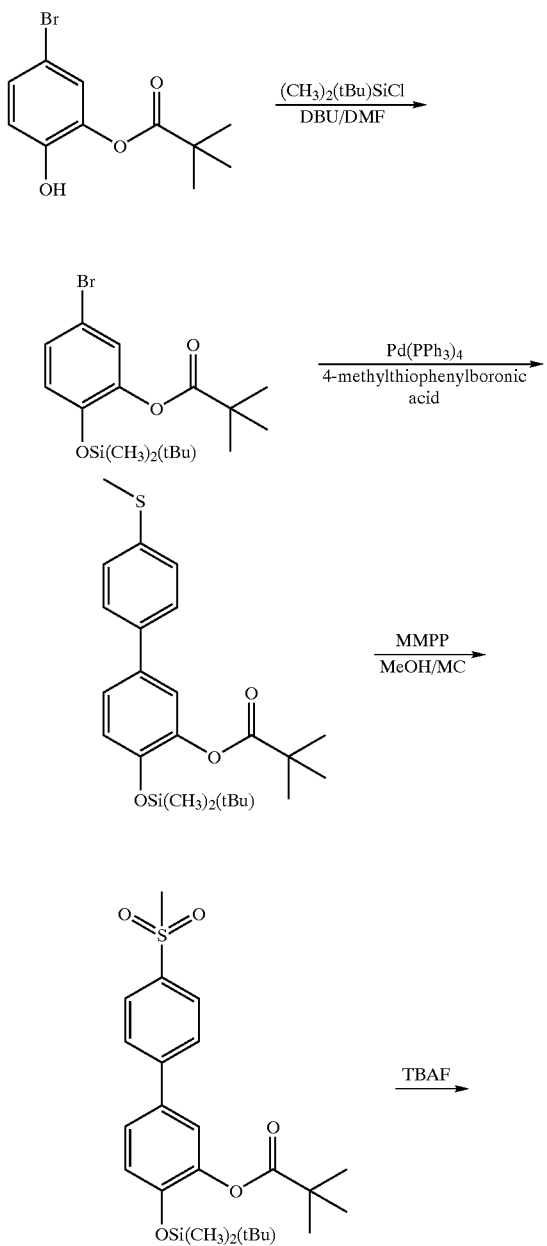

seceded in the process of hydrolyzing methanesulfonyl group which has been formed onto 4'-location of biphenyl and then, diol compound is formed. By reacting diol compound with $R^x$ compound, a compound where $R^1$ and $R^2$ are identical is obtained.

After completing the reaction, the resulting products can be processed through a common treatment such as chromatography, re-crytallization and the like so as to be separated and purified.

The compound of the present invention depicted in formula 1 has an activity for the selective inhibition against cyclooxygenase-2 and thus can be utilized as an enzymatic inhibitor. The compound of formula 1 as a selective inhibitor against cyclooxygenase-2 can be a substitute for conventional non-steroid anti-inflammatory drugs. Concretely, it improves side effects of anti-inflammatory drugs in existed non-steroids and is useful in patients suffering from peptic ulcer, gastritis, partial enteritis, ulcerative colitis, diverticulitis, gastrointestinal haemorrhagia, hypoprothrombinemia and the like. Besides, it is expected to treat inflammatory diseases such as osteoarthritis, rheumatoid arthritis and the like effectively.

The compound of the present invention can be administered in a single dose or in separated doses, depending upon clinical purposes. The specific dosage for patients will vary, depending upon factors such as a sort of drug compound, body weight, sex, physical condition, diet, administration period, administration method, discharge ratio, drug composition and severity of diseases and the like.

The compound of the present invention can be administered as an oral, a local, a parenteral (subcutaneous, venous and muscular syringe or injection), an inhalational or a rectal drug. In case that these are prepared to a pharmaceutical drug, one or more commonly used vehicles, methods for the preparation and the like can be adopted properly from prior arts widely reported to those skilled.

In order to attain the desired purpose of clinical administration, the active compound of formula 1 in the present invention can be administered coincidently by combining more than one component of other commercial drugs.

However, the pharmaceutical drugs containing the compound of the present invention is not limited to forms described above, if it has a purpose for inhibiting cyclooxygenase-2 selectively. All kinds of drugs useful for the enzymatic inhibition can be within the scope of the present invention.

MODES FOR CARRYING OUT THE INVENTION

Practical and presently preferred embodiments of the present invention are illustrated as shown in the following Examples.

However, it will be appreciated that those skilled in the art, on consideration of this disclosure, may make modifications and improvements within the spirit and scope of the present invention.

REFERENCE EXAMPLE 1

Preparation of 2,2-Dimethylpropionic Acid 2-Hydroxyphenylester

Cathechol (10 g) with NaH (3.64 g) was dissolved in dimethylformamide and then, stirred for 30 minutes at 0° C. Pivaloylchloride (6 ml) was added to the above suspension and stirred for 1 hour at room temperature. After completing the reaction, water was added to dilute and extracted with ethylacetate. An organic layer was dried over anhydrous magnesium sulfate, distilled by reducing pressure, and separated by performing a silica gel attributed chromatography (an eluting agent: ethylacetate/n-hexane=1/4, v/v). As a result, the present compound (8.7 g, productive yield 50%) was obtained as an oil phase.

$^1$H-NMR (400 MHz, CDCl$_3$) δ 6.93 (t, 1H, J=2 Hz), 6.87 (d, 1H, J=8 Hz), 6.83 (d, 1H, J=8 Hz), 1.21 (s, 9H);

$^{13}$C-NMR (100 MHz, CDCl$_3$) δ 177.6, 147.6, 139.5, 126.7, 122.6, 121.5, 118.4, 39.8, 27.4.

REFERENCE EXAMPLE 2

Preparation of 2,2-Dimethylpropionic Acid 5-Bromo-2-hydroxyphenylester 2,2 dimethylpropionic acid 2-hydroxyphenylester (6 g) was dissolved in dichloromethane and bromine (4 ml) was added slowly at 0° C. Then, the blended solution was reacted for 30 minutes at −75° C. After completing the reaction, sodium thiosulfate was added to remove bromine, water was added to dilute, and extracted with ethylacetate. A resulting organic layer was dried over anhydrous magnesium sulfate and distilled under reduced pressure. As a result, the present compound (2.2 g, productive yield 97%) was obtained as a white solid.

$^1$H-NMR (400 MHz, CDCl$_3$) δ 7.06 (d, 1H, J=4 Hz), 7.04 (s, 1H), 6.71 (d, 1H, J=4 Hz), 5.15 (s, 1H);

$^{13}$C-NMR (100 MHz, CDCl$_3$) δ 177.3, 146.9, 140.0, 130.2, 125.8, 120.2, 112.6, 39.8, 27.5.

REFERENCE EXAMPLE 3

Preparation of 2,2-Dimethylpropionic Acid 5-Bromo-2-t-butyldimethylsilyloxyphenylester 2,2-dimethylpropionic acid 5-bromo-2-hydroxyphenylester (2 g) was mixed with imidazole (1.6 g) as a base and dimethylaminopyridine (50 mg) as a catalyst and dissolved in dimethylformamide. T-butyldimethylsilylchlroride (1.2 g) was added to the produced solution and stirred for 2 hours at room temperature. After completing the reaction, water was added to dilute and extracted with ethylacetate. A resulting organic layer was dried over anhydrous magnesium sulfate, distilled under reduced pressure, and separated through a silica gel attributed chromatography (n-hexane). As a result, the present compound (2.2 g, productive yield 71%) was obtained.

$^1$H-NMR (400 MHz, CDCl$_3$) δ 7.05 (d, 1H, J=4 Hz), 7.03 (s, 1H), 6.83 (d, 1H, J=4 Hz), 1.33 (s, 9H), 0.97 (s, 9H), 0.25 (s, 6H);

$^{13}$C-NMR (100 MHz, CDCl$_3$) δ 176.5, 148.9, 144.7, 129.6, 124.7, 118.70, 112.81, 39.40, 27.71, 26.11, 18.74, −3.78.

REFERENCE EXAMPLE 4

Preparation of 2,2-Dimethylpropionic Acid 4-(t-Butyldimethylsilyloxy)-4'-methanesulfanyl-biphenyl-3-ilester 2,2-dimethylpropionic acid 5-bromo-2-t-butyldimethylsilyloxyphenylester (200 mg) was mixed with 4-methylthiophenylboronic acid (130 mg) and tetrakistriphenylphospinepalladium (6 mg) as a catalyst. Then, the blended solution was dissolved in dried toluene (3 ml), ethanol (1 ml), and 2M potassium carbonate (0.7 ml) and refluxed for 4 hours. Water was poured to the above suspend to dilute and extracted with dichloromethane. A separated organic layer was dried over anhydrous magnesium sulfate, distilled under reduced pressure, and separated through a silica gel attributed chromatography (an eluting agent: dimethylether/petroleum ether=1/30, v/v). As a result, the present compound (140 mg, productive yield 64%) was obtained.

$^1$H-NMR (400 MHz, CDCl$_3$) δ 7.48–7.41 (m, 2H), 7.34–7.28 (m, 2H), 7.28–7.25 (m, 1H), 7.14–6.93 (m, 2H), 2.50 (s, 3H), 1.38 (s, 9H), 1.00 (s, 9H), 0.27 (s, 6H).

REFERENCE EXAMPLE 5

Preparation of 2,2-Dimethylpropionic Acid 4-t-Butyldimethylsilyloxy-4'-methanesulfonyl-biphenyl-3-ilester 2,2-dimethylpropionic acid 4-(t-butyldimethylsilyloxy)-4'-methanesulfanyl-biphenyl-3-ilester (70 mg) was mixed with dichloromethane and methanol (5/1, v/v) and dissolved. Thereafter, magnesium monoperoxyphthalate hexahydrate (164 mg) was added and reacted at room temperature. After reacting for 2 hours, sodium hydrogen carbonate solution and salt solution were added and extracted with dichloromethane. An obtained organic layer was dried over anhydrous magnesium sulfate and distilled under reduced pressure. Then, the residue was separated through a silica gel attributed chromatography (an eluting agent: methylacetate/petroleum ether=1/30, v/v). As a result, the present compound (64 mg, productive yield 84%) was obtained.

$^1$H-NMR (400 MHz, CDCl$_3$) δ 8.01–7.95 (m, 2H), 7.75–7.67 (m, 2H), 7.41–7.10 (m, 3H), 3.09 (s, 3H), 1.42 (s, 9H);

melting point: 68~70° C.

REFERENCE EXAMPLE 6

Preparation of 4'-Methanesulfonyl-biphenyl-3,4-diol 2,2-dimethylpropionic acid 4-(t-butyldimethylsilyloxy)-4'-methanesulfonyl-biphenyl-3-ilester (120 mg) was dissolved in tetrahydrofuran and reacted with tetrabutylammoniumfluoride (TBAF; 0.34 ml) at 0° C. The reacted solution was heated up to room temperature and stirred for one hour. Then, the reaction was completed over ammonium chloride solution. Afterward, salt water was added to dilute and extracted with dichloromethane. An obtained organic layer was dried over anhydrous magnesium sulfate and distilled under reduced pressure. The residue was separated through a silica gel attributed chromatography (an eluting agent: methylacetate/petroleum ether=1/3, v/v). As a result, the present compound (80 mg, productive yield 90%) was obtained.

$^1$H-NMR (400 MHz, CDCl$_3$) δ 7.93 (d, 2H, J=8.6 Hz), 7.79 (d, 2H, J=8.6 Hz), 7.13 (d, 1H, J=2.3 Hz), 7.06 (dd, 1H, J=8.2Hz, 2.3 Hz), 6.87 (d, 1H, J=8.6 Hz), 3.8–3.3 (bs, 2H), 3.21 (s, 3H);

melting point: 204~206° C.

REFERENCE EXAMPLE 7

Preparation of 2,2-Dimethylpropionic Acid 5-Bromo-2-isopropyloxy-phenylester 2,2-dimethylpropionic acid 5-bromo-2-hydroxyphenylester (500 mg) was dissolved in dimethylformamide and stirred with 1,8-diazabicyclo[5.4.0]undece-7-ene (DBU; 0.32 ml) for 10 minutes. Then, 2-bromopropane (0.25 ml) was added and heated at 40° C. After the reaction was completed, water was added to dilute and extracted with ethylacetate. An organic layer was dried over anhydrous magnesium sulfate, filtered, and distilled under reduced pressure. The residue was separated through a silica gel attributed chromatography (an eluting agent: ethylacetate/n-hexane=1/12, v/v). As a result, the present compound (340 mg, productive yield 60%) was obtained.

$^1$H-NMR (400 MHz, CDCl$_3$) δ 7.06 (s, 1H), 7.03 (d, 1H, J=8 Hz), 6.87 (d, 1H, J=8 Hz), 4.48 (s, 1H), 1.34 (s, 9H), 1.32 (s, 3H), 1.31 (s, 3H);

$^{13}$C-NMR (100 MHz, CDCl$_3$) δ 176.5, 150.7, 140.7, 124.5, 123.7, 119.3, 73.4, 39.4, 27.6, 22.5.

EXAMPLE 1

Preparation of 4'-Methanesulfonyl-3,4-dimethoxy-biphenyl

4'-methanesulfonyl-biphenyl-3,4-diol (30 mg) and potassium carbonate (38 mg) were dissolved in methylethylketone. Afterward, methane iodide (0.021 ml) was added and refluxed for 3 hours at 100° C. After filtering just potassium carbonate, the residue was separated through a silica gel attributed chromatography (an eluting agent: ethylacetate/n-hexane=1/4, v/v). As a result, the present compound (22 mg, productive yield 60%) was obtained.

$^1$H-NMR (400 MHz, CDCl$_3$) δ 7.93 (d, 2H, J=8.6 Hz), 7.79 (d, 2H, J=8.6 Hz), 7.13 (d, 1H, J=8.2 Hz, 2.3 Hz), 7.06 (d, 1H, 2.3 Hz), 6.87 (d, 1H, J=8.2 Hz), 3.97 (s, 3H), 3.94 (s, 3H), 3.21 (s, 3H);

$^{13}$C-NMR (100 MHz, CDCl$_3$) δ 150.3, 149.9, 146.9, 139.0, 132.3, 128.3, 127.9, 120.5, 112.1, 110.9, 56.5, 56.5, 46.1;

Mass (FAB) 293.1 (M+1).

EXAMPLE 2

Preparation of 4'-Methanesulfonyl-3,4-diethoxy-biphenyl

4'-methanesulfonyl-biphenyl-3,4-diol (30 mg) and potassium carbonate (38 mg) were dissolved in methylethylketone. Afterward, ethane iodide (0.027 ml) was added and refluxed for 3 hours at 100° C. After filtering just potassium carbonate, the residue was separated through a silica gel attributed chromatography (an eluting agent: ethylacetate/n-hexane=1/1, v/v). As a result, the present compound (20 mg, productive yield 67%) was obtained.

$^1$H-NMR (400 MHz, CDCl$_3$) δ 7.93 (d, 2H, J=8.6 Hz), 7.79 (d, 2H, J=8.6 Hz), 7.13 (dd, 1H, J=8.2 Hz, 2.3 Hz), 7.06 (d, 1H, J=2.3 Hz), 6.87 (d, 1H, J=8.2 Hz), 4.16 (q, 4H, J=2 Hz), 3.21 (s, 3H), 1.48 (t, 3H, J=2 Hz);

$^{13}$C-NMR (100 MHz, CDCl$_3$) δ 150.3, 149.9, 146.9, 139.0, 132.4, 128.3, 127.9, 120.5, 112.1, 110.9, 54.5, 45.1, 15.3;

Mass (FAB) 320.1 (M+1).

EXAMPLE 3

Preparation of 4'-Methanesulfonyl-3,4-dipropyloxy-biphenyl

4'-methanesulfonyl-biphenyl-3,4-diol (30 mg) and potassium carbonate (38 mg) were dissolved in methylethylketone. Afterward, propane iodide (0.032 ml) was added and refluxed for 3 hours at 100° C. After filtering just potassium carbonate, the residue was separated through a silica gel attributed chromatography (an eluting agent: ethylacetate/n-hexane=1/1, v/v). As a result, the present compound (30 mg, productive yield 90%) was obtained.

$^1$H-NMR (400 MHz, CDCl$_3$) δ 7.93 (d, 2H, J=8.6 Hz), 7.79 (d, 2H, J=8.6 Hz), 7.13 (dd, 1H, J 8.2 Hz, 2.3 Hz), 7.06 (d, 1H, 2.3 Hz), 6.87 (d, 1H, J=8.2 Hz), 4.03 (q, 4H), 3.21 (s, 3H), 1.87 (q, 4H, J=2 Hz), 1.09 (t, 3H, J=2 Hz);

$^{13}$C-NMR (100 MHz, CDCl$_3$) δ 150.3, 149.9, 146.9, 139.0, 132.3, 128.3, 127.9, 120.5, 112.2, 110.9, 56.5, 45.1, 30.1, 1.41;

Mass (FAB) 349.21 (M+1).

EXAMPLE 4

Preparation of 4'-Methanesulfonyl-3,4-diisopropyloxy-biphenyl

4'-methanesulfonyl-biphenyl-3,4-diol (30 mg) and potassium carbonate (38 mg) were dissolved in methylethylketone. Afterward, 2-bromopropane (0.062 ml) was added and heated for 24 hours at 40° C. After filtering just potassium carbonate, the residue was separated through a silica gel attributed chromatography (an eluting agent: ethylacetate/n-hexane=1/1, v/v). As a result, the present compound (28 mg, productive yield 85%) was obtained.

$^1$H-NMR (400 MHz, CDCl$_3$) δ 7.93 (d, 2H, J=8.6 Hz), 7.79 (d, 2H, J=8.6 Hz), 7.13 (dd, 1H, J=8.2 Hz, 2.3 Hz), 7.06 (d, 1H, J=2.3 Hz), 6.87 (d, 1H, J=8.2 Hz), 4.53 (m, 1H), 3.21 (s, 3H), 1.37 (s, 6H), 1.36 (s, 6H);

$^{13}$C-NMR (100 MHz, CDCl$_3$) δ 149.3, 148.3, 145.4, 137.5, 131.4, 126.8, 126.5, 120.1, 116.9, 116.7, 71.8, 71.1, 43.6, 28.7, 21.3, 21.2;

melting point: 123~125° C.

EXAMPLE 5

Preparation of 4'-Methanesulfonyl-3,4-dicyclopropyloxy-biphenyl

4'-methanesulfonyl-biphenyl-3,4-diol (30 mg) and potassium carbonate (38 mg) were dissolved in methylethylketone. Afterward, bromocyclopropane (0.027 ml) was added and heated for 24 hours at 40° C. After filtering just potassium carbonate, the residue was separated through a silica gel attributed chromatography (an eluting agent: ethylacetate/n-hexane=1/1, v/v). As a result, the present compound (29 mg, productive yield 87%) was obtained.

$^1$H-NMR (400 MHz, CDCl$_3$) δ 7.98 (d, 2H, J=8 Hz), 7.73 (d, 2H, J=8 Hz), 7.22 (s, 1H), 7.11 (dd, 1H, J=8 Hz, 4 Hz), 7.09 (d, 1H, J=4 Hz), 6.97 (d, 1H, J=8 Hz), 6.20–6.17 (m, 1H), 6.16–6.13 (m, 1H), 5.46 (dd, 1H, J=16 Hz, 2 Hz), 5.45 (dd, 1H, J=16 Hz, 2 Hz), 5.37 (dd, 1H, J=8 Hz, 2 Hz), 5.35 (dd, 1H, J=8 Hz, 2 Hz), 3.08 (s, 3H).

EXAMPLE 6

Preparation of 4'-Methanesulfonyl-3,4-dibutyloxy-biphenyl

4'-methanesulfonyl-biphenyl-3,4-diol (30 mg) and potassium carbonate (38 mg) were dissolved in methylethylketone. Afterward, butane iodide (0.038 ml) was added and heated for 24 hours at 40° C. After filtering just potassium carbonate, the residue was separated through a silica gel attributed chromatography (an eluting agent: ethylacetate/n-hexane=1/1, v/v). As a result, the present compound (35 mg, productive yield 90%) was obtained.

$^1$H-NMR (400 MHz, CDCl$_3$) δ 7.97 (d, 2H, J=6.8 Hz), 7.72 (d, 2H, J=6.8 Hz), 7.16 (dd, 1H, J=8.2 Hz, 2.2 Hz), 7.13 (d, 1H, J=2.2 Hz), 6.98 (d, 1H, J=8.2 Hz), 4.15–3.96 (m, 4H), 3.08 (s, 3H), 1.92–1.85 (m, 4H), 1.75–1.47 (m, 5H), 1.10–0.95 (m, 5H);

melting point: 123~125° C.

EXAMPLE 7

Preparation of 4'-Methanesulfonyl-3,4-dibenzyloxy-biphenyl

4'-methanesulfonyl-biphenyl-3,4-diol (30 mg) and potassium carbonate (38 mg) were dissolved in methylethylketone. Afterward, benzylbromide (60 mg) and tetrabutylammoniumiodide (2–3 mg) were added one after another and heated for 24 hours at 40° C. After filtering just potassium carbonate, the residue was separated through a silica gel attributed chromatography (an eluting agent: ethylacetate/n-hexane=1/1, v/v). As a result, the present compound (42 mg, productive yield 85%) was obtained.

$^1$H-NMR (400 MHz, CDCl$_3$) δ 7.96 (d, 2H, J=8.7 Hz), 7.64 (d, 2H, J=8.7 Hz), 7.52–7.44 (m, 4H), 7.42–7.35 (m, 4H), 7.34–7.27 (m, 2H), 7.19 (d, 1H, J=2.2 Hz), 7.15 (dd, 1H, J=8.3 Hz, 2.2 Hz), 7.03 (d, 1H, J=8.3 Hz), 5.30 (s, 4H), 3.07 (s, 3H);

melting point: 175~177° C.

EXAMPLE 8

Preparation of 4'-Methanesulfonyl-3,4-dicyclopentyloxy-biphenyl

4'-methanesulfonyl-biphenyl-3,4-diol (30 mg) and potassium carbonate (38 mg) were dissolved in methylethylketone. Afterward, cyclopentylbromide (51 mg) and tetrabutylammoniumiodide (2–3 mg) were added one after another and heated for 24 hours at 40° C. After filtering just potassium carbonate, the residue was separated through a silica gel attributed chromatography (an eluting agent: ethylacetate/n-hexane=1/1, v/v). As a result, the present compound (37 mg, productive yield 92%) was obtained.

$^1$H-NMR (400 MHz, CDCl$_3$) δ 7.96 (d, 2H, J=8.5 Hz), 7.72 (d, 2H, J=8.5 Hz), 7.16 (dd, 1H, J=8.1 Hz, 2.2 Hz), 7.14(d, 1H, J=2.2 Hz), 6.97 (d, 1H, J=8.1 Hz), 4.90–4.72 (m, 2H), 3.01 (s, 3H), 2.10–1.82 (m, 12H), 1.80–1.50 (m, 4H);

melting point: 147~149° C.

EXAMPLE 9

Preparation of 3-Butoxy-4-isopropoxy-4'-methanesulfonyl-biphenyl 4-isopropoxy-4'-methanesulfonyl-biphenyl-3-ol (30 mg) and potassium carbonate (20 mg) were dissolved in methylethylketone. Afterward, butane iodide (27 mg) and tetrabutylammoniumiodide (2–3 mg) was added one after another and heated for 24 hours at 40° C. After filtering just potassium carbonate, the residue was separated through a silica gel attributed chromatography (an eluting agent: ethylacetate/n-hexane=1/1, v/v). As a result, the present compound (30 mg, productive yield 88%) was obtained.

$^1$H-NMR (400 MHz, CDCl$_3$) δ 8.03 (d, 2H, J=8 Hz), 7.75 (d, 2H, J=8 Hz), 7.19 (dd, 1H, J=4 Hz, 2 Hz), 7.16 (d, 1H, J=2 Hz), 7.15 (d, 1H, J=4 Hz), 4.72 (s, 1H), 3.98 (t, 2H, J=2 Hz), 2.99 (s, 3H), 1.74–1.48 (m, 2H), 1.48–1.47 (m, 2H), 1.31 (s, 3H), 1.30 (s, 3H), 1.19 (s, 3H).

EXPERIMENTAL EXAMPLE

The Activity of Selective Inhibition Against Cyclooxygenase-2

(1) Experimental Procedure

In order to investigate the activity of the present compound for the selective inhibition against cyclooxygenase-2 enzyme pharmacologically, the enzymatic activities inhibiting cyclooxygenase-1 and cyclooxygenase-2 were measured quantitatively.

First of all, the cyclooxygenase-1 was examined through the following procedure.

Peritoneal fluid in which macrophages were suspended was extracted from a mouse peritoneal cavity and centrifuged at 4° C., 1,000 rpm for 2 minutes. Then, the supernatant was removed, suspended using 20 ml of incomplete RPMI medium [including PC/SM (penicilin/streptomycin)] and again centrifuged under the same condition. In addition, the reactant was washed twice and then the cell pellet was suspended with 10 ml of incomplete RPMI 1640 medium so as to prepare a cell suspension. Then, the cell number was calculated with the hemocytometer and adjusted to reach $1 \times 10^6$ cells/ml of cell concentration in the final cell suspension. The resulting suspension was poured into each well of 96-well plate and left with the incubator at 37° C. in 5% $CO_2$ for about 2 hours in order to attach macrophages. The attached macrophage was washed twice by using PBS buffer, treated to experimental samples in a proper concentration and then blended with 3% FBS-RPMI 1640 medium so as to adjust the total volume reaching 200 $\mu$l. The resulting cell was cultivated with the incubator at 37° C. in 5% $CO_2$ for about 12~16 hours. Then, arachidonic acid was added, adjusting to 10 $\mu$M of a final concentration and incubated at 37° C. for more 10 minutes and the supernatant of the reacted solution (~180 $\mu$l) was recovered to finish the reaction. In order to quantitate the amount of PGE2 in the samples, the ELISA method recommended from Cayman Chemical company was exploited and the obtained results was used to estimate the inhibition ratio (%) of each compound against cyclooxygenase-1.

Second, the cyclooxygenase-2 was examined through the following procedure.

Peritoneal fluid in which macrophages were suspended was extracted from a mouse peritoneal cavity and centrifuged at 4° C., 1,000 rpm for 2 minutes. Then, the supernatant was removed, suspended using 20 ml of incomplete RPMI medium [PC/SM (penicilin/streptomycin)] and again centrifuged under the same condition. In addition, the reactant was washed twice and then the cell pellet was suspended with 10 ml of incomplete (without serum) RPMI 1640 medium so as to prepare a cell suspension. Then, the cell number was calculated with the hemocytometer and adjusted to reach $1 \times 10^6$ cells/ml of cell concentration in the final cell suspension. The resulting suspension was treated with aspirin, adjusting 500 $\mu$M of final concentration and poured into each well of 96-well plate in 100 $\mu$l respectively. Again, it was left with the incubator at 37° C. in 5% $CO_2$ for about 2 hours in order to attach macrophages. The attached macrophage was washed twice by using PBS buffer, treated to experimental samples in a proper concentration and then blended with 3% FBS-RPMI 1640 medium containing 10 $\mu$g/ml of LPS in each well. The resulting cell was cultivated with the incubator at 37° C. in 5% $CO_2$ for about 12~16 hours. Then, arachidonic acid was added, adjusting to 10 $\mu$M of a final concentration and incubated at 37° C. for more 10 minutes and the supernatant of the reacted solution (~180 $\mu$l) was recovered to finish the reaction. In order to quantitate the amount of PGE2 in the samples, the ELISA method recommended from Cayman Chemical company was exploited and the obtained results was used to estimate the inhibition ratio (%) of each compound against cyclooxygenase-2.

(2) Experimental Results

The experimental results were demonstrated in Table 1 as follows.

Table 1

Inhibitory effects of cyclooxygenase (COX) (unit: % inhibition)

| Examples | COX-1 | | | COX-2 | | |
|---|---|---|---|---|---|---|
| Concentration | 30 $\mu$M | 10 $\mu$M | 3 $\mu$M | 300 nM | 100 nM | 30 nM |
| SC-58635 (standard substance) | 81.3 | 66.5 | 64.3 | 73.0 | 59.9 | 51.2 |
| 1 | 64.7 | 50.5 | 44.4 | 59.7 | 50.7 | 46.2 |
| 2 | 77.1 | 70.5 | 61.5 | 76.5 | 60.5 | 55.2 |
| 3 | 23.4 | 10.1 | 9.4 | 10.1 | 5.5 | 5.0 |
| 4 | 78.4 | 70.4 | 58.2 | ~0 | ~0 | ~0 |
| 5 | 60.4 | 58.4 | 50.3 | 46.5 | 33.3 | 30.2 |
| 6 | 22.7 | 20.9 | 14.7 | ~0 | ~0 | ~0 |
| 7 | 41.1 | 40.5 | 36.8 | 68.4 | 60.3 | 47.6 |
| 8 | 49.7 | 40.2 | 29.7 | 54.7 | 42.7 | 27.4 |
| 9 | 70.8 | 66.4 | 49.8 | 70.4 | 59.8 | 44.2 |

In vitro experiments were observed to measure the inhibitional ratios against cyclooxygenase-1 (COX-1) and cyclooxygenase-2 (COX-2). Consequently, in case of the compound of Example 2, 4'-methanesulfonyl-3,4-diethoxy-biphenyl, the inhibition effect against clooxgenase-2 was identified to be more excellent than a comparative substance and coincidently, the inhibiton on effect against cyclooxygenase-1 be in much lower level than a comparative substance. That is to say, the selectivity of cyclooxygenase-2 is confirmed to be better than any other substances, which proves the structural efficacy of 4'-methanesulfonyl-biphenyl derivatives in the present invention.

INDUSTRIAL APPLICABILITY

As demonstrated and confirmed above, the novel compound of 4'-methanesulfonyl-biphenyl derivative is a drug substitute improving side effects of anti-inflammatory drug in existed non-steroids and is useful for patients suffering from peptic ulcer, gastritis, partial enteritis, ulcerative colitis, diverticulitis, gastrointestinal haemorrhagia, hypoprothrombinemia and the like. Besides, it is expected to treat inflammatory diseases such as osteoarthritis, rheumatoid arthritis and the like effectively.

Those skilled in the art will appreciate that the conceptions and specific embodiments disclosed in the foregoing description may be readily utilized as a basis for modifying or designing other embodiments for carrying out the same purposes of the present invention.

Those skilled in the art will also appreciate that such equivalent embodiments do not depart from the spirit and scope of the invention as set forth in the appended claims.

What is claimed is:

1. A compound of formula 1 and its pharmaceutically acceptable salts:

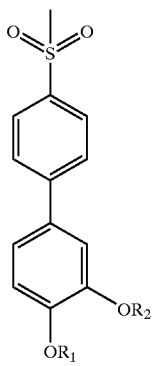

Formula 1

Wherein, $R^1$ and $R^2$ are respectively a hydrogen;

$C_1$–$C_4$-alkyl substituted or not substituted by halogens;

$C_3$–$C_7$-cycloalkyl;

$C_1$–$C_5$-alkyl containing 1~3 ether bonds and/or an aryl substitute;

substituted or not substituted phenyl;

or substituted or not substituted five or six ring-cycled heteroaryl containing more than one hetero atoms selected from a group consisting of nitrogen, sulfur and oxygen (wherein, phenyl or heteroaryl can be one- or multi-substituted by a substituent selected from a group consisting of hydrogen, methyl, ethyl and isopropyl).

2. The compound of formula 1 according to claim 1, wherein $R^1$ and $R^2$ are respectively selected from a group consisting of:

methyl; ethyl; propyl; isopropyl; butyl; cyclopropyl; cyclopentyl; and benzyl.

3. The compound according to claim 1, wherein said compound of formula 1 is selected from a group consisting of:

4'-methanesulfonyl-3,4-dimethoxy-biphenyl;
4'-methanesulfonyl-3,4-diethoxy-biphenyl;
4'-methanesulfonyl-3,4-dipropyloxy-biphenyl;
4'-methanesulfonyl-3,4-diisoprophyloxy-biphenyl;
4'-methanesulfonyl-3,4-dicyclopropyloxy-biphenyl;
4'-methanesulfonyl-3,4-dibutyloxy-biphenyl;
4'-methanesulfonyl-3,4-dibenzyloxy-biphenyl;
4'-methanesulfonyl-3,4-dicyclopentyloxy-biphenyl; and
3-butoxy-4-isopropoxy-4'-methanesulfonyl-biphenyl.

* * * * *